United States Patent [19]

Slanetz, Jr.

[11] Patent Number: 5,257,999
[45] Date of Patent: Nov. 2, 1993

[54] SELF-ORIENTED LAPAROSCOPIC NEEDLE HOLDER FOR CURVED NEEDLES

[76] Inventor: Charles A. Slanetz, Jr., 107 Ayer Rd., Locust Valley, N.Y. 11560

[21] Appl. No.: 893,276

[22] Filed: Jun. 4, 1992

[51] Int. Cl.$^5$ ............................................. A61B 17/00
[52] U.S. Cl. ...................................................... 606/147
[58] Field of Search ................................ 606/147, 207

[56] References Cited

U.S. PATENT DOCUMENTS

| | | | |
|---|---|---|---|
| 253,209 | 2/1882 | Jones | 606/147 |
| 453,698 | 6/1891 | Hoeller | 606/147 |
| 695,292 | 3/1902 | Ermold | 606/147 |
| 1,266,456 | 5/1918 | Greely | 606/147 |
| 1,327,577 | 1/1920 | Turner | 606/147 |
| 1,445,348 | 2/1923 | Noble | 606/147 |
| 1,704,992 | 3/1929 | Sanders | 606/147 |
| 2,795,225 | 6/1957 | Sovatkin et al. | 606/147 |
| 3,120,847 | 2/1964 | Cavaness | 606/147 |
| 4,226,240 | 10/1980 | Walker, Jr. | |
| 4,226,241 | 10/1980 | Walker, Jr. | |
| 4,491,135 | 1/1985 | Klein | 606/147 |
| 4,597,390 | 7/1986 | Mulhollan et al. | 606/148 |
| 4,693,246 | 9/1987 | Reimels | 606/147 |
| 4,793,349 | 12/1988 | Weinrib | 606/147 |
| 4,898,157 | 2/1990 | Messroghli et al. | 606/147 |
| 4,961,742 | 10/1990 | Torre | 606/147 |
| 5,100,421 | 3/1992 | Christoudias | 606/147 |

FOREIGN PATENT DOCUMENTS 625598 8/1961 Canada .
242254 2/1911 Fed. Rep. of Germany .

OTHER PUBLICATIONS

Cook Incorporated Publication, "Endoscopic Curved Needle Driver", OECS291 (1991).

Primary Examiner—Stephen C. Pellegrino
Assistant Examiner—Gary Jackson
Attorney, Agent, or Firm—Hoffmann & Baron

[57] ABSTRACT

A self-orienting laparoscopic needle holder having a shaft suitably sized for laparoscopy. The shaft has a jaw assembly at one end and a mechanism for opening and closing the jaws at the other end. The gripping surfaces of the jaws are curved to correspond to the curve of a curved surgical needle. One jaw has a convex shape while the other jaw has a corresponding concave shave. The shape of the curved gripping surfaces of the jaws automatically orients the curved surgical needle into a desired suturing position. The shape of the jaw assembly also makes it possible to easily release and regrasp the curved surgical needle during the suturing process of a laparoscopic operation.

18 Claims, 4 Drawing Sheets

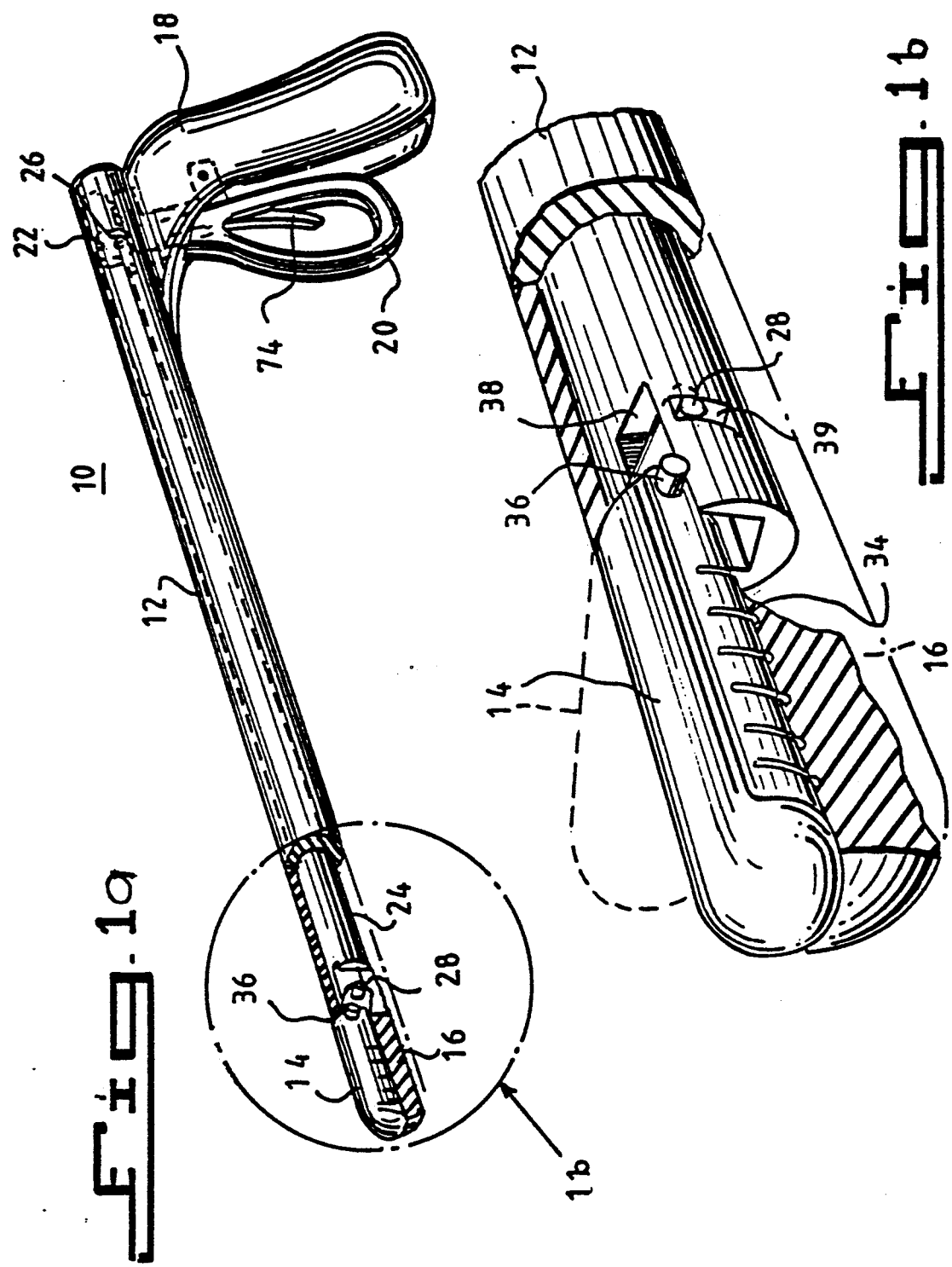

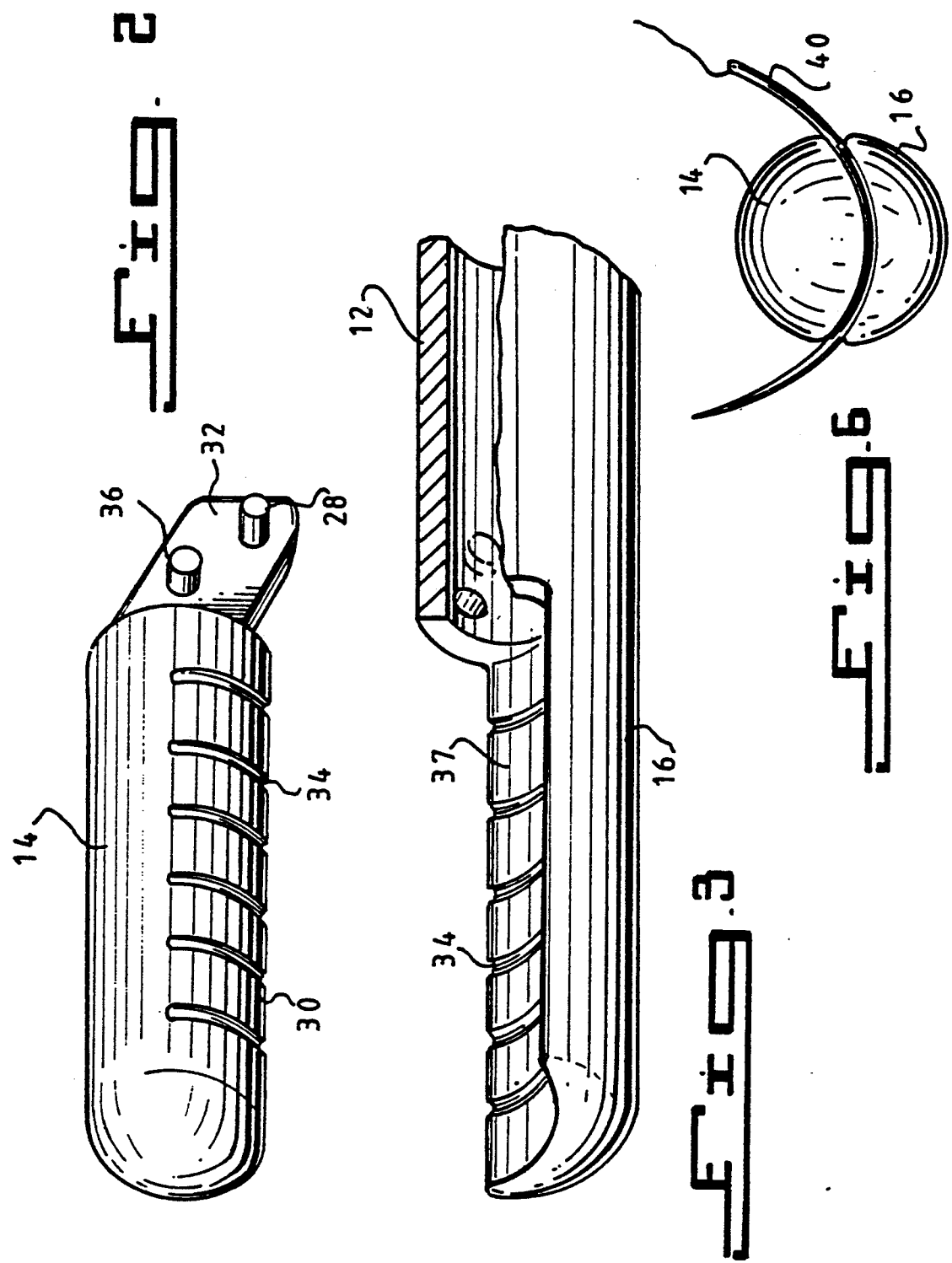

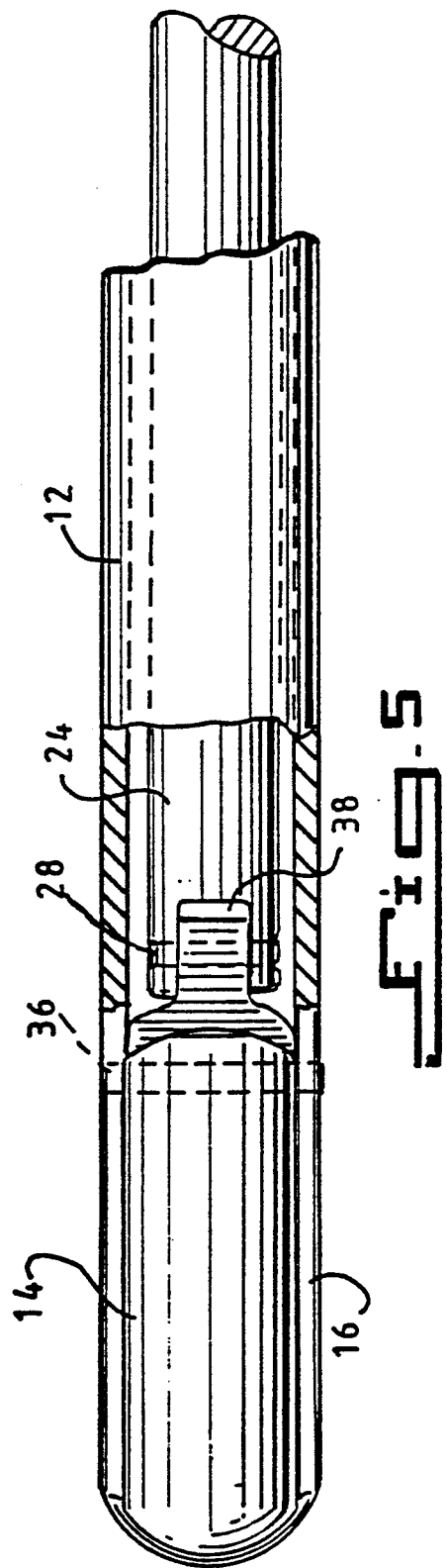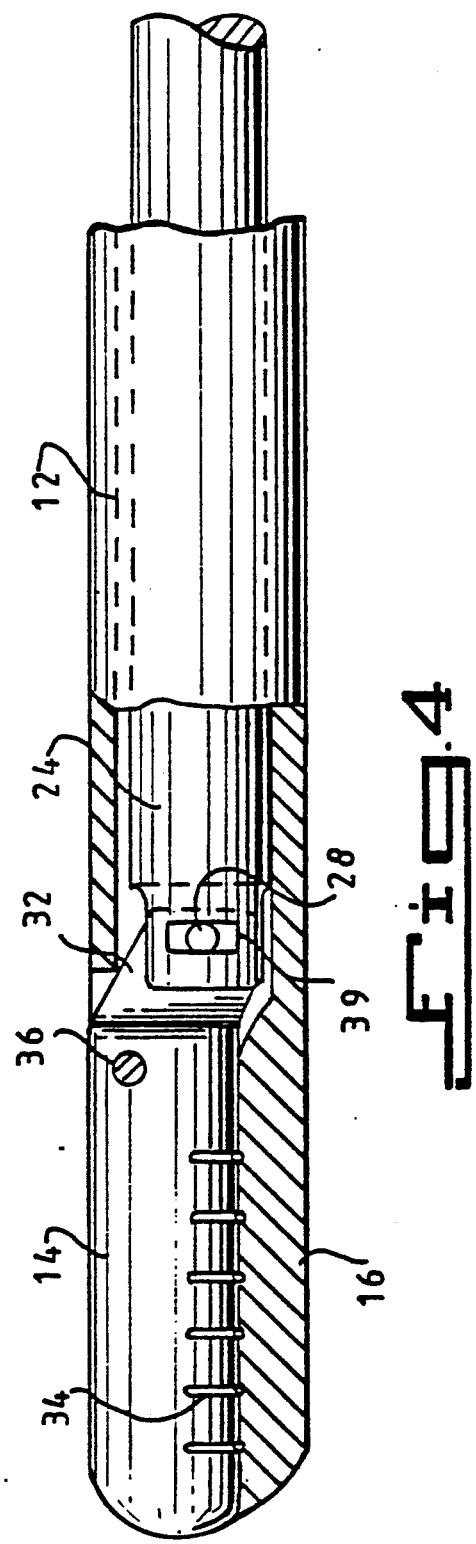

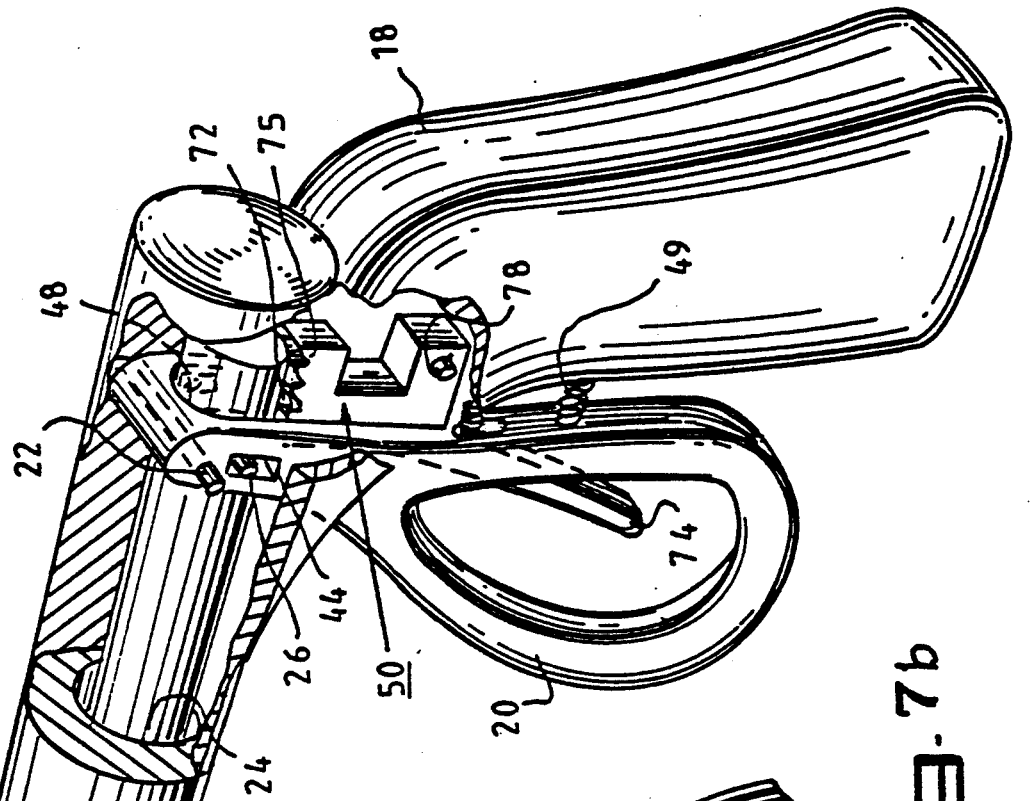
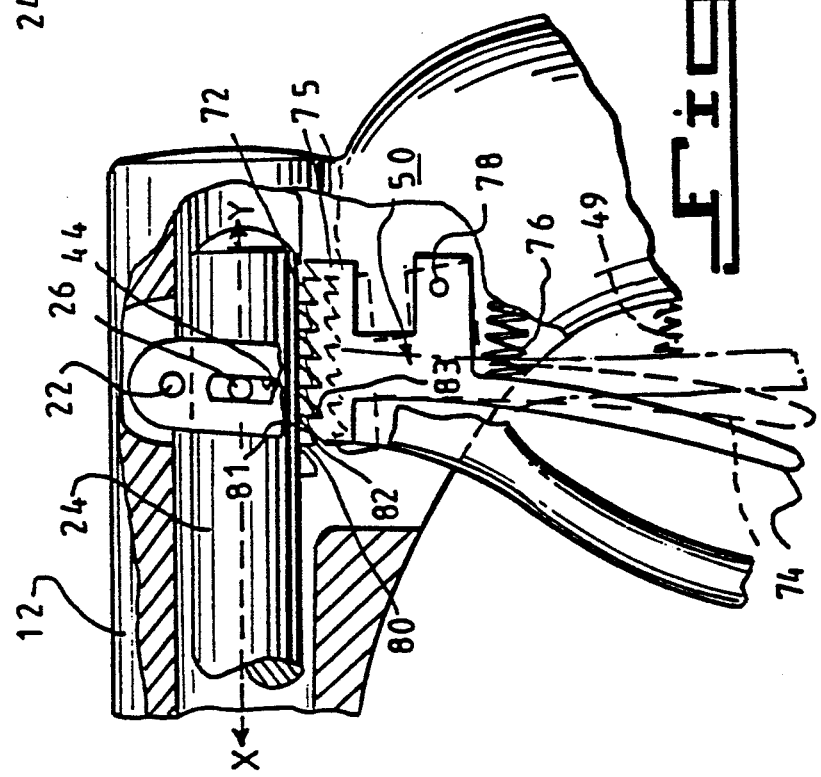

SELF-ORIENTED LAPAROSCOPIC NEEDLE HOLDER FOR CURVED NEEDLES

BACKGROUND OF THE INVENTION

1. Field of the Invention

The present invention relates to surgical instruments and more particularly to an improved laparoscopic instrument for use in manipulating a curved needle in an area of limited access.

2. Background of the Related Art

Laparoscopy is the examination and surgical treatment of the interior of the abdomen by means of a laparoscope. The laparoscope is an instrument comparable to an endoscope, which is introduced surgically through the abdominal wall for examining the intra-abdominal organs. The most common uses of laparoscopy are for diagnosis of intra-abdominal diseases and for operations that require cholecystectomy, hernia repairs, adhesiolysis, hysterectomy, oophoresectomy, colectomy, and many other surgical procedures.

Various laparoscopic procedures involve the cutting and suturing of internal tissue. The suturing in laparoscopic procedures is difficult since the needle must be manipulated in an area of limited access with only two dimensional views. It is important that the curved needle commonly used in these procedures is maintained in the proper orientation in order to facilitate suturing. Also, the needle must be held securely because as needles enter tissues, they are often deflected sideways and turned.

Various instruments have been designed to accomplish these requirements, however, each contains disadvantages inherent in their design making them difficult to use. For example, U.S. Pat. No. 4,597,390 discloses a surgical needle manipulator. This device includes a tube with a telescopic rod inside the tube. Both the tube and rod have a diametrical slot at one end forming a bifurcated slot. The tube and rod are relatively rotatable resulting in the two slots being movable in and out of alignment. When the slots are in alignment, the shank of the needle can be received in the slots. As the slots are moved out of alignment, the needle is grasped by the side walls of the slots. This instrument, however, does not provide a very secure means for grasping the needle. Also, it is difficult in the confined work space to place the needle in the diametrical slots at the end of the tube and rod to facilitate grasping the needle. If the needle is inadvertently released or dropped within the patient, it is virtually impossible to pick up the needle with this instrument or replace it in the proper orientation. Also, while attempting to retrieve the needle with this instrument inside of the body cavity of the patient the surgeon may damage surrounding tissues.

In a Cook Incorporated publication, OECS291 (1991), an "Endoscopic Curved Needle Driver" is disclosed. This device consists of a long hollow cylindrical shaft with a "U" shaped handle at one end and a needle holding section at the other. At the handle end is a rotatable knob which secures the needle within the needle holding section. The Cook device also has a design which makes it difficult to re-grasp a needle during the suturing process. The needle holding section is made up of a grooved area near the end of the cylindrical shaft. If the needle is dropped, or its orientation has been changed while inside of the patent it would be virtually impossible to retrieve or reposition the needle with this device. Also, the needle holding section is positioned a small distance (about 1–2 cm) from the tip of the cylindrical shaft. Tissue surrounding the area to be sutured may be damaged by the protrusion of the cylindrical shaft beyond the point at which the needle is held.

Similarly, U.S. Pat. No. 3,871,379 discloses a combined laparoscopic needle and forceps consisting of an elongated parallelogram type linkage, means for mounting a needle at the end of the device and a forcep construction including a jaw mounted proximate to the holder for the needle. This patent also discloses a similar device in which the jaw contains a groove associated with the jaws for receiving a suture to act as a suture guide, and a cutting means mounted on the jaws for cutting a suture. The parallelogram construction of the '379 patent does not allow this device to be used within a laparoscopic tube, nor does it provide a secure grip on the suture needle. Also, if the suture needle is dropped, the design does not facilitate retrieving the needle.

U.S. Pat. No. 4,491,135 discloses a surgical needle holder for curved needles comprised of movable gripping jaws offset from a manipulating handle by a distance substantially equal to the radius of curvature of the surgical needle. The device uses a parallelogram type of linkage to open and close the jaws. The linkage and offset jaws are too large to fit within a surgiport during laparoscopic surgery and therefore cannot be utilized in such procedures.

Curved needle holders for external surgical procedures have been disclosed in U.S. Pat. No. 697,292; U.S. Pat. No. 1,445,348; and U.S. Pat. No. 3,120,847. Each of these patents discloses a scissor or forcep configuration containing a groove or notch in the jaws of the instrument. The notch of the '292 patent prevents breakage of the needle due to the pressure exerted by the jaws. The grooves of the '348 and '847 patents allow griping of the needle such that the needle may be oriented in a variety of positions to facilitate suturing. Since the scissor or forcep configuration is used, each of these surgical instruments are specifically designed for external surgical procedures. The handles of these instruments cannot fit within a laparoscopic tube and therefore cannot be used for laparoscopic suturing. If these instruments were used for internal surgical procedures they may cause ripping or tearing of the surrounding tissue due to the width of the handles.

Therefore, based on existing instrumentation for laparoscopic surgery, there is a need for a laparoscopic instrument which (1) can easily grasp a needle, release the needle, and again grasp the needle, even if the needle is accidently dropped by the surgeon (2) orients the needle in the upright position to facilitate suturing, and (3) provides maximum holding pressure when holding the suture.

It is therefore a purpose of the present invention to provide a laparoscopic instrument which self-orients a curved surgical needle in an upright position to facilitate ease in suturing.

Another purpose of the present invention is to provide a laparoscopic instrument which can easily grasp, release, and re-grasp a curved surgical needle and place the needle in a correct orientation for suturing.

Still another purpose of the present invention is to provide a laparoscopic needle holding instrument with a substantial mechanical advantage with respect to the force applied to the instrument handles and the resulting force applied at the instrument jaws to securely hold the curved surgical needle.

A further purpose of the present invention is to provide a new method of suturing in laparoscopic surgery utilizing the self-orienting laparoscopic needle holder for curved needles.

Yet another purpose of the present invention is to provide a self-orienting laparoscopic needle holder instrument which is easy to manufacture, yet is strong and durable.

Another purpose of the present invention is to provide an improved laparoscopic instrument which enhances the ability to suture during laparoscopy.

It is a further purpose of the present invention to provide a self-orienting laparoscopic curved needle holder which is easily manipulated by one hand and is rapidly engageable and disengageable.

SUMMARY OF THE INVENTION

These and further goals and purposes are achieved by the present invention which provides a self-orienting laparoscopic needle holder for curved needles. The preferred laparoscopic needle holding device for grasping and manipulating a curved surgical needle includes a shaft suitably sized for laparoscopy. The shaft must fit within a laparoscopic tube used during a laparoscopic procedure. The shaft has an upper and lower jaw at one end of the shaft. Preferably, at least one of the jaws is pivotally coupled to the shaft. The jaws also have a curved gripping surface, one of the jaw's gripping surface has a convex shape while the other jaw's gripping surface has a corresponding concave shape. These curved surfaces preferably contain a plurality of corresponding transverse grooves. These grooves facilitate the receiving, orienting and securely gripping of a curved surgical needle within the jaws of the laparoscopic needle holding device. Also, the jaws should be preferably rounded at the tips, as well as having a cylindrical outer shape corresponding to the shape of the shaft, when the jaws are in a closed position.

The laparoscopic needle holding device of the present invention also includes a mechanism for pivotally opening and closing the jaws of the device. The mechanism for selectively opening and closing the jaws is preferably positioned at the end of the shaft opposite the jaws. When the mechanism is actuated closing the jaws in order to hold a curved surgical needle, the shape of the jaws' curved gripping surfaces automatically orients the curved surgical needle into a desired suturing position.

The self-orienting laparoscopic needle holder of the present invention also preferably includes a locking device. When the locking device is engaged, the jaws are selectively maintained in a closed position. When the locking device is disengaged, the upper and lower jaws can be selectively positioned between and open and closed position. The open position is preferably maintained by a spring or other biasing mechanism.

The laparoscopic needle holding device of the present invention is preferably made from a biocompatible material since it will be used inside the human body. Suitable biocompatible materials such as stainless steel and tungsten carbide may be used, however, various other materials such as plastics and composites are also suitable.

The method of using the self-orienting laparoscopic needle holder includes gripping the curved surgical needle in the jaws of the device and inserting the laparoscopic needle holder and needle through a laparoscopic operating tube. After insertion, the curved surgical needle can be manipulated by grasping, releasing, and regrasping the needle during the suturing process. Each time the curved surgical needle is grasped, the needle is automatically oriented into a desired suturing position. Upon completion of suturing, the needle and the self-orienting laparoscopic needle holder are withdrawn from the laparoscopic operating tube.

For a better understanding of the present invention, reference is made to the following description and examples in conjunction with the accompanying figures, the scope of which is pointed out in the appended claims.

BRIEF DESCRIPTION OF THE DRAWINGS

FIG. 1a is a side elevational view of the laparoscopic device of the present invention; FIG. 1b is an enlarged view of the jaw assembly shown in FIG. 1a.

FIG. 2 is a side perspective view of the upper jaw component of the laparoscopic device of the present invention.

FIG. 3 is a side perspective view of the lower jaw component of the present invention.

FIG. 4 is a side perspective view of the jaw assembly illustrating the coupling of the upper jaw to the shaft and travel rod.

FIG. 5 is a top elevational partial cutaway view of the jaw assembly illustrating the coupling arrangement for the upper jaw to the shaft and travel rod.

FIG. 6 is a front elevational view of the jaw assembly holding a curved surgical needle.

FIG. 7a is a side perspective partial cutaway view showing the assembly of the movable and fixed handles and locking mechanism of the laparoscopic needle holder of present invention; FIG. 7b is a side elevational partial cutaway view showing the assembly of the movable and fixed handles and locking mechanism of the laparoscopic needle holder of the present invention shown in FIG. 7a.

DETAILED DESCRIPTION OF THE PREFERRED EMBODIMENTS

A preferred self-orienting laparoscopic needle holder 10 for holding curved needles in accordance with the present invention is illustrated in FIGS. 1a and 1b. The preferred laparoscopic needle holder 10 has a hollow fixed shaft 12 with an upper 14 and lower 16 jaw, respectively, at the first end of the shaft 12. At the second end of shaft 12 is a fixed handle 18. The fixed handle 18 is preferably oriented substantially perpendicular to the hollow fixed shaft 12. A movable handle 20 is coupled near its top, preferably using a pin 22, to the shaft 12 at its second end, proximal to the top of the fixed handle 18. The movable handle 20 is also coupled to a travel rod 24, preferably by a pin 26, which is positioned within the hollow shaft 12.

The travel rod 24 can be longitudinally displaced along the longitudinal central axis of the hollow shaft 12. The travel rod 24 is coupled to the upper jaw 14, preferably using a pin 28, at one end, and is coupled to the movable handle 20, preferably using pin 26, at the opposite end.

The upper jaw 14 is illustrated in greater detail in FIGS. 1b and 2. The upper jaw 14 has an outer gripping surface 30 and an upper jaw leg 32. The outer gripping surface 30 is semi-circular and convex in shape, and it may contain either slots 34 or a roughened surface to facilitate grasping a curved surgical needle. The upper jaw leg 32 is coupled to the travel rod 24 by a pin 28. The upper jaw 14 is coupled by pin 36 to the hollow shaft 12 at its fulcrum. The fulcrum of the upper jaw 14 is positioned approximately where the outer gripping surface 15 and the upper jaw leg 32 meet.

Referring to FIG. 3, the lower jaw 16 which preferably makes up the terminal end of the hollow fixed shaft 12, has a concave semi-circular inner gripping surface 37 corresponding to the convex outer gripping surface 30 of the upper jaw 14. The lower and upper jaws, 16 and 14 respectively, also preferably contain corresponding slots 34 to facilitate grasping of a curved surgical needle. Another embodiment of the present invention may contain a roughened surface on the upper and lower jaws, 14 and 16 respectively, rather than the slots 34. FIG. 3 also illustrates the hole in the hollow shaft 12 for insertion of pin 36 which holds the upper jaw 14 at its fulcrum.

The coupling assembly of the upper jaw 14 to the hollow fixed shaft 12 and travel rod 24, as well as the arrangement of the upper jaw 14 with respect to the lower jaw 12 are illustrated in FIGS. 4 and 5. FIG. 4 is a side perspective view of the jaw assembly. The travel rod 24 is coupled to the upper jaw leg 32 by pin 28. As shown in FIG. 5, the travel rod 24 has a first slot 38 at its end proximal to jaws 14, 16 to accommodate the upper jaw leg 32. The travel rod 24 also contains a second vertical slot 39 around coupling pin 28 to allow for the vertical travel of the coupling pin 28 when the travel rod 24 is longitudinally displaced along the longitudinal central axis of the fixed hollow shaft 12. As the travel rod 24 is longitudinally displaced by the movement of the movable handle 20, the upper jaw 14 is pivotally moved toward the lower jaw 16 to a closed position. When the laparoscopic needle holder 10 is operated and the jaws 14, 16 are moved to the closed position, a curved surgical needle 40 is automatically oriented and firmly grasped between the respective gripping surfaces 30 and 37 of the upper and lower jaws 14, 16 as illustrated in FIG. 6.

FIG. 5 is a top elevational partial cutaway view showing the arrangement of the pins coupling the upper jaw 14 to the fixed hollow shaft 12 and the travel rod 24. The length of the coupling pin 28 is equal to the width of the travel rod 24, to allow the travel rod 24 to be longitudinally displaced within the hollow fixed shaft 12. The length of coupling pin 36 is approximately equal to the cross-sectional width of the hollow fixed shaft 12 at the point of attachment of the upper jaw 14.

FIG. 6 is a front elevational end view of the jaw assembly 14, 16 in the closed position. The jaw assembly 14, 16 has a circular cross-sectional shape in order to allow the laparoscopic needle holder 10 to be used within a laparoscopic tube. FIG. 6 also shows that the upper and lower jaw, 14 and 16, respectively, have corresponding convex and concave shapes to facilitate grasping and automatically orientating a curved surgical needle 40 to the correct upright position.

As can be seen in FIGS. 1, 5 and 6 the tip of the closed jaw assembly 14, 16 of the laparoscopic needle holder 10 is substantially smooth and has a semi-spherical rounded shape. The substantially smooth, semi-spherical rounded shape helps to prevent tissue damage to surrounding tissue when suturing. There are no points or edges which may rip or tear surrounding tissues during the laparoscopic suturing procedure.

FIGS. 7a and 7b are partial cutaway views showing the assembly of the movable 20 and fixed 18 handles as well as a locking mechanism for the laparoscopic needle holder 10. The movable handle 20 is coupled to both the hollow fixed shaft 12 and the travel rod 24. The movable handle 20 is coupled to the hollow fixed shaft 12 by a pin 22 located near the top of the movable handle 20. The movable handle 20 is loosely coupled to the end of the travel rod 24 by another coupling pin 26. The movable handle 20 contains a vertical slot 44 for surrounding coupling pin 26 to allow for the travel of the coupling pin 26 when the movable handle 20 is moved in relation to the fixed handle 18.

The movable handle 20 may be maintained in an open position by a spring 49 or other biasing means. The spring 49 or biasing means is illustrated as positioned between movable handle 20 and fixed handle 18, although it may also be positioned internal to the handles of the laparoscopic needle holder 10. In the open position, the jaws 14, 16 of the laparoscopic needle holder 10 are pivotally separated from each other. When the laparoscopic needle holder 10 is in the open position the spring 49 or other biasing means maintains the separation of movable handle 20 from the fixed handle 18.

As shown in FIGS. 7a and 7b, the laparoscopic needle holder 10 of the present invention also preferably includes a locking mechanism 50 which can maintain the jaws 14, 16 and handles 18, 20 in either the open or closed position. After the locking mechanism 50 is engaged, the surgeon need not apply pressure to the handles to maintain the jaws 14, 16 in the closed position. The locking mechanism 50 is automatically engaged to hold the needle securely in place between the jaws. Preferably, as shown in FIGS. 7a and 7b, the locking mechanism 50 is disengaged by applying pressure to a trigger 74 positioned preferably in a slot 48, formed in the movable handle 20, thereby releasing the locking mechanism 50.

The preferred locking mechanism 50 includes a plurality of traveling teeth 72, from about 1-12 teeth, preferably 4-6 teeth, formed on the bottom of the travel rod 24 at the end proximal to the movable handle 20 and a trigger assembly 74 having corresponding locking teeth 75, from about 1 to 12 teeth, preferably 3-6 teeth, which interlock with the traveling teeth 72. The trigger assembly 74 and travel rod 24 are positioned within a slot 48 formed within the movable handle 20. The trigger assembly 74 is pivotally coupled to the fixed handle 18 by a coupling pin 78.

As shown in FIG. 7b, each of the traveling teeth 72 have at least two surfaces 80, 81 for engaging two corresponding surfaces 82, 83 respectively, on the locking teeth 75. The outer surfaces 80 on the traveling teeth 72 are oriented at approximately a 90° or an acute angle as measured in relation to the longitudinal central axis, X-Y, of the travel rod 24 as illustrated in FIG. 7b. The other surfaces 81 of the traveling teeth 72 are oriented at an obtuse angle, specifically an angle greater than 90° and less than 180°, preferably between 120° and 145°, as measured in relation to the longitudinal central axis X-Y of the travel rod. The outer surfaces 82, 83 of the locking teeth 75 are preferably oriented in the opposite direction as the respective surfaces 80, 81 of the traveling teeth 72 to create an interlocking engagement between the teeth 72, 75 surfaces.

The locking mechanism 50 is designed to automatically engage as the moveable handle 20 is pulled toward the fixed handle 18, causing the travel rod 24 to be pulled in the Y-direction, thereby bringing the jaws 14, 16 to a closed position. The trigger assembly 74 is biased away from the fixed handle 18 by a spring 76 maintaining the traveling teeth 72 and the locking teeth 75 in interlocking contact of surfaces 80 and 83, respectively, thereby locking the jaws 14, 16 in a closed position. The traveling teeth 72 are formed so that the outer surfaces 81 are permitted to ratchet over outer surfaces 82 of the locking teeth 75 when the travel rod 24 is moved in the Y-direction to close the jaws 14, 16. Therefore, the traveling and locking teeth, 72 and 75 respectively, automatically engage to place the jaws in a locked position after movable handle 20 has been moved toward the fixed handle 18, moving the travel rod 24 in the Y-direction.

To release the locking mechanism 50, the trigger 74 of the locking mechanism 50 is pulled in a direction towards the fixed handle 18. Since the trigger assembly 74 is pivotally coupled to the fixed handle 18 by coupling pin 78, the locking teeth 75 of the trigger assembly 74 are pulled down and away from the traveling teeth 72 thereby releasing the travel rod 24 and allowing the jaws 14, 16 to be opened.

Other locking mechanisms may include, but are not limited to a ratchet locking means positioned between the handles of the device or a push-button type of locking mechanism. The details for constructing such locking mechanisms are well known to those skilled in the art.

The movable handle 20 may be designed in a variety of ways as well known to those skilled in the art. In the preferred embodiment 10 of the present invention shown in FIGS. 1 and 7, the movable handle 20 has an opening large enough for a surgeon to place four fingers within the handle. In another embodiment of the present invention (not shown) the movable handle may be solid, with contours corresponding to the fingers of the surgeon.

The laparoscopic needle holder 10 of the present invention is preferably made from a biocompatible material since it will be used inside the human body. The preferred embodiment of the present invention is preferably made from stainless steel but other suitable materials such as tungsten carbide and various other materials such as plastics and composites may also be used.

Now referring to FIGS. 1a and 1b, in order to grasp a curved surgical needle using the laparoscopic needle holder 10 of the present invention, the means for pivotally opening and closing the jaws 14, 16 is operated to selectively position the jaws 14, 16 in either the open or closed position. In the preferred embodiment illustrated in FIGS. 1a and 1b, when pressure is applied to the movable handle 20 in a direction towards the fixed handle 18 the jaws will close due to the coupling of movable handle 20 to travel rod 24 and the coupling of the travel rod 24 to jaws 14, 16. The travel rod 24 is pulled longitudinally along the central axis of the hollow fixed shaft 12 in the direction towards the fixed handle. The travel rod 24, coupled to the upper jaw leg 32 at its opposite end, pivots the upper jaw 14 towards the lower jaw 16 and into a closed position.

Upon closing the jaws 14, 16, a curved surgical needle 40 placed between the jaws will be self-oriented into a proper position by the curvature of the jaws' gripping surfaces 30, 37, in order to facilitate suturing. The laparoscopic needle holder 10 of the present invention is designed so that a curved surgical needle 40 may be easily grasped, released, and regrasped. Each time the needle is grasped, it is placed in the desired orientation, [for example, concave up with the point facing upwards] for the surgeon. The orientation of the curved gripping surfaces of the jaws 30, 37 may be adapted so that other desirable orientations of the curved needles can be achieved, for example concave down, curve left or right, depending on the preference of the surgeon.

Thus, while I have described what are the presently contemplated preferred embodiments of the present invention, further changes and modifications could be made by those skilled in the art without departing from the scope of the invention, and it is contemplated to claim all such changes and modifications.

I claim:

1. A laparoscopic needle holding device for grasping and manipulating a curved surgical needle, comprising:
   a shaft suitably sized for laparoscopy, wherein said shaft is hollow along its length, said shaft having at a first end an upper and lower jaw, one of said jaws being pivotally coupled to said shaft, said jaws having a curved gripping surface, wherein one of said jaw's gripping surface has a convex shape and the other said jaw's gripping surface has a corresponding concave shape; and
   means for opening and closing said jaws operable through said hollow shaft, said opening and closing means being positioned proximal to a second end of said shaft opposite said jaws, said means for opening and closing said jaws, comprises:
   (a) a travel rod which moves longitudinally along a longitudinal central axis of said hollow shaft, said travel rod being coupled to said pivotally mounted jaw at said first end of said hollow shaft, said travel rod being coupled to a movable handle at said second end of said hollow shaft, said movable handle pivotally coupled to said hollow shaft; and
   (b) a fixed handle at said second end of said hollow shaft; whereby when said jaws are closed, said shaft, said means for opening and closing said jaws and said jaws present a substantially smooth outer surface along the length of the shaft, and the shape of the interacting gripping surfaces of the jaws automatically orients said curved surgical needle into a desired suturing position.

2. A laparoscopic needle holding device according to claim 1, wherein one of said curved gripping surfaces contains a transverse groove, sad groove adapted for receiving, orienting and securely gripping a curved surgical needle.

3. A laparoscopic needle holding device according to claim 1, wherein one of said curved gripping surfaces has a roughened surface adapted for receiving, orienting and securely gripping a curved surgical needle.

4. A laparoscopic needle holding device according to claim 1, wherein the curved gripping surfaces are substantially semi-circular to correspond to the curvature of a curved surgical needle.

5. A laparoscopic needle holding device according to claim 1, wherein one of said jaws is contiguous with said first end of the shaft.

6. A laparoscopic needle holding device according to claim 5, wherein the other of said jaws is pivotally coupled to said shaft proximal to a fulcrum of said jaw.

7. A laparoscopic needle holding device according to claim 1, wherein when said jaws are in a closed position, they combine to present a substantially smooth, spherical rounded exterior surface.

8. A laparoscopic needle holding device according to claim 1, further comprising a handle positioned proximal to said second end of said shaft.

9. A laparoscopic needle holding device according to claim 1, further comprising a biasing means disposed between said movable handle and said fixed handle to provide a force to urge said handles apart and said jaws in an open position.

10. A laparoscopic needle holding device according to claim 1, further comprising a locking means for fixing said jaws in a closed position.

11. A laparoscopic needle holding device according to claim 1, further comprising a locking means for selectively maintaining said jaws in a closed position, said locking means comprising:
  a traveling tooth formed on the travel rod at said second end proximal to said movable handle, said traveling tooth having an engaging surface and a sliding surface;
  a trigger assembly including a trigger having a first end which extends through an opening in said movable handle and a locking tooth at a second end of said trigger, the locking tooth having a locking surface for contacting the engaging surface of said traveling tooth thereby locking the position of the travel rod.

12. A laparoscopic needle hodling device according to claim 11, wherein said trigger assembly is pivotally coupled to the fixed handle between said first end and said second end of said trigger thereby allowing said locking tooth to engage said traveling tooth and lock said travel rod, and for allowing said locking tooth to be selectively disengaged from said traveling tooth to release said travel rod; and
    said sliding surface of said traveling tooth is oriented at an obtuse angle as measured in relation to a longitudinal central axis of said travel rod, whereby the sliding surface of said traveling tooth can ratchet over the locking tooth when the travel rod is moved along said longitudinal central axis in a direction toward the fixed handle to close the jaws.

13. A laparoscopic needle holding device according to claim 1, further comprising a biasing means to urge said jaws to an open position.

14. A laparoscopic needle holding device according to claim 1 wherein said device is fabricated from materials selected from the group consisting of stainless steel, tungsten carbide, plastics, composites and combinations thereof.

15. A laparoscopic needle holding device for grasping and manipulating a curved surgical needle, comprising:
  a shaft suitably sized for laparoscopy said shaft is hollow along its length, said shaft having at a first end an upper and lower jaw, one of said jaws being pivotally coupled to said shaft, said jaws having a curved gripping surface, wherein one of said jaw's gripping surface has a convex shape and the other said jaw's gripping surface has a corresponding concave shape;
  means for opening and closing said jaws, said opening and closing means being positioned proximal to a second end of said shaft opposite said jaws, said means for opening and closing said jaws, comprises:
    (a) a travel rod which moves longitudinally along a longitudinal central axis of said hollow shaft, said travel rod being coupled to said pivotally mounted jaw at said first end of said hollow shaft, said travel rod being coupled to a movable handle at said second end of said hollow shaft, said movable handle pivotally coupled to said hollow shaft; and
    (b) a fixed handle at said second end of said hollow shaft;
  whereby when said jaws are closed said shaft, said means for opening and closing said jaws, and said jaws present a substantially smooth outer surface along the length of the shaft, and the shape of the interacting gripping surfaces of the jaws automatically orients said curved surgical needle into a desired suturing position; and
  a locking means for selectively locking said jaws in a closed position wherein said locking means, comprises:
    a plurality of traveling teeth formed on the travel rod at said second end proximal to said movable handle, said traveling teeth having an engaging surface and a sliding surface;
    a trigger assembly including a trigger having a first end which extends through an opening in said movable handle and a locking tooth at a second end of said trigger, the locking tooth having a locking surface for contacting the engaging surface of said traveling teeth, said trigger assembly is pivotally coupled to the fixed handle between said first end and said second end of said trigger thereby allowing said locking tooth to engage said traveling teeth and lock said travel rod, and for allowing said locking tooth to be selectively disengaged from said traveling teeth to release said travel rod.

16. A laparoscopic needle holding device according to claim 15, wherein said locking means includes a biasing means to maintain the engaging surface of said traveling teeth in contact with the locking surface of said locking tooth;
  said sliding surfaces of said traveling teeth are oriented at an obtuse angle as measured in relation to a longitudinal central axis of said travel rod, whereby the sliding surface of said traveling teeth can ratchet over the locking tooth when the travel rod is moved along said longitudinal central axis in a direction toward the fixed handle to close the jaws.

17. A method of suturing during laparoscopic surgery utilizing a self-orienting needle holder, the method comprises:
  (a) gripping a curved surgical needle between a jaw assembly of a self-orienting laparoscopic needle holder wherein said surgical needle is automatically oriented into a desired position for suturing, said self-orienting laparoscopic needle holder includes a shaft suitably sized for laparoscopy wherein said shaft is hollow along its length, said shaft having at a first end said jaw assembly having an upper and lower jaw, one of said jaws being pivotally coupled to said shaft, said jaws having a curved gripping surface, wherein one of said jaw's gripping surface having a convex shape and the other said jaw's gripping surface having a corresponding concave shape and means for opening and closing said jaws, said opening and closing means being positioned proximal to a second end of said shaft opposite said jaws,
    said means for opening and closing said jaws, comprises:

(i) a travel rod which moves longitudinally along a longitudinal central axis of said hollow shaft, said travel rod being coupled to said pivotally mounted jaw at said first end of said hollow shaft, said travel road being coupled to a movable handle at said second end of said hollow shaft, said movable handle pivotally coupled to said hollow shaft; and (ii) a fixed handle at said second end of said hollow shaft, whereby when said jaws are closed said shaft, said means for opening and closing said jaws, and said jaws present a substantially smooth outer surface, and the shape of the interacting gripping surfaces of the jaws automatically orients said curved surgical needle into a desired suturing position;

(b) inserting said self-orienting laparoscopic needle holder gripping said curved surgical needle through a laparoscopic operating tube;

(c) manipulating said self-orienting needle holder by grasping, releasing and regrasping said curved surgical needle during the suturing procedure whereby each time said curved surgical needle is grasped in said jaw assembly of said self-orienting laparoscopic needle holder, the needle is automatically oriented into a desired position for suturing; and (d) removing said self-orienting laparoscopic needle holder while gripping said curved surgical needle from said laparoscopic operating tube.

18. A laparoscopic needle holding device for grasping and manipulating a curved surgical needle, comprising:

a shaft suitably sized for laparoscopy, wherein said shaft is hollow along its length, said shaft having at a first end an upper and lower jaw, one of said jaws being pivotally coupled to said shaft, said jaws having a curved gripping surface, wherein one of said jaw's gripping surface has a convex shape and the other said jaw's gripping surface has a corresponding concave shape; and means for opening and closing said jaws operable through said hollow shaft, said opening and closing means being positioned proximal to a second end of said shaft opposite said jaws, whereby when said jaws are closed, said shaft, said means for opening and closing said jaws and said jaws present a substantially smooth outer surface along the length of the shaft, and the shape of the interacting gripping surfaces of the jaws automatically orients said curved surgical needle into a desired suturing position.

* * * * *